United States Patent [19]

McAleer et al.

[11] 4,273,762
[45] Jun. 16, 1981

[54] LYOPHILIZATION PROCESS FOR LIVE VIRAL COMPOSITIONS

[75] Inventors: William J. McAleer, Ambler; Henry Z. Markus, Wyncote, both of Pa.

[73] Assignee: Merck & Co., Inc., Rahway, N.J.

[21] Appl. No.: 99,772

[22] Filed: Dec. 3, 1979

[51] Int. Cl.³ .................. A61K 39/12; A61K 39/165
[52] U.S. Cl. .................................. 424/89; 435/235; 435/238; 34/5
[58] Field of Search ................... 424/89; 34/5; 435/235–239

[56] References Cited

U.S. PATENT DOCUMENTS

| | | | |
|---|---|---|---|
| 3,078,215 | 2/1963 | Fantes | 424/89 |
| 3,132,073 | 5/1964 | MacFarlane et al. | 424/89 |
| 3,183,161 | 5/1965 | McClean et al. | 424/89 |
| 3,197,374 | 7/1965 | Hennessen et al. | 424/89 |
| 3,316,153 | 4/1967 | Van Frank | 424/89 |
| 3,478,145 | 11/1969 | Lapidus | 424/89 |
| 3,509,070 | 4/1970 | Lapidus | 424/89 |
| 3,555,149 | 1/1971 | Buynak et al. | 424/89 |
| 3,608,071 | 9/1971 | Relyveld et al. | 424/89 |
| 3,629,399 | 12/1971 | Mauler et al. | 424/89 |
| 3,783,098 | 1/1974 | Calnek et al. | 424/89 |
| 3,915,794 | 10/1975 | Zygraich et al. | 424/89 |
| 3,933,585 | 1/1976 | McAleer et al. | 424/89 |
| 3,961,046 | 6/1976 | Cerini | 424/89 |
| 4,147,772 | 4/1979 | McAleer et al. | 424/89 |

*Primary Examiner*—Shep K. Rose
*Attorney, Agent, or Firm*—Donald J. Perrella; Hesna J. Pfeiffer

[57] ABSTRACT

Lyophilization time of live viral compositions is reduced and output per lyophilization unit is increased by lyophilizing a reduced volume of a more concentrated viral composition.

6 Claims, No Drawings

LYOPHILIZATION PROCESS FOR LIVE VIRAL COMPOSITIONS

BACKGROUND OF THE INVENTION

Aqueous solutions of live vaccines are known to be unstable. The conventional technique to reduce instability is to remove water by lyophilization. Lyophilization, however, is time consuming, energy intensive, and requires the use of very expensive equipment. The major factor controlling the time and expense of lyophilization is the amount of water to be removed. Prior art attempts to reduce lyophilization time and expense by increasing concentration failed due to precipitation of suspension medium ingredients.

OBJECTS OF THE INVENTION

It is, accordingly, an object of the present invention to provide a shorter and less expensive lyophilization method for live viral compositions. Another object is to provide precipitate-free viral compositions having reduced volume and increased concentration. These and other objects of the present invention will be apparent from the following description.

SUMMARY OF THE INVENTION

Lyophilization time of live viral compositions is reduced and output per lyophilization unit is increased by lyophilizing a reduced volume of a more concentrated viral composition wherein phosphate salt is added as a final step.

DETAILED DESCRIPTION

The present invention relates to the lyophilization of live viral compositions and, more particularly, to an improved process for reducing lyophilization time and expense of live viral vaccines.

A single dose vaccine, e.g. of measles, conventionally is prepared by lyophilizing a volume of about 0.5–0.7 ml, plus slight overfill, of diluted viral concentrate having a solids content after dilution of about 75–80 mg/ml. The lyophilization time takes up to 40 hours. A ten dose vial containing 7 ml of the same concentrate requires up to 160 hours for lyophilization. The diluent contains ingredients intended to stabilize the virus including a phosphate salt. Attempts to shorten the lyophilization time by reducing the water content and thus increasing the concentration have been unsuccessful due to the formation of a precipitate.

The formulation of stabilizer-containing diluents is known in the art. A commonly used stabilizer SPGA, described by Bovarnick et al., J. Bact. 59: 509–522 (1950) contains 0.218 M sucrose, 0.0038 M monopotassium phosphate, 0.0072 M dipotassium phosphate, phosphate, 0.0049 M monosodium glutamate, and 1% bovine albumin powder. An improved stabilizer containing a 6-carbon polyhydric alcohol, partially hydrolyzed gelatin, a cell culture medium and an acidic buffer is described in U.S. Pat. No. 4,147,772.

It has now been found that precipitation may be avoided if the diluent is formulated in a manner wherein the phosphate salt is added as the final step. Such a diluent permits formation of more concentrated solutions which do not form precipitates and which can be lyophilized in reduced time. By a more concentrated solution is meant one which before lyophilization contains less than about 75% of its reconstituted volume after lyophilization. The phosphate salt may be added to the diluent as the final ingredient or the diluent without its phosphate salt may be added to the concentrated virus, and the diluent then added as the final ingredient.

The following examples illustrate the present invention without, however, limiting the same thereto.

EXAMPLE 1

A measles virus concentrate (720 ml) having a titer of $10^4$ TCID$_{50}$/0.1 ml which has been stored at $-70°$ C. is thawed in a water bath at 25° C. and then diluted fourfold to produce a viral fluid titering $10^{3.4}$ TCID$_{50}$/0.1 ml. Each liter of the diluent liquid contains the following:

Partially hydrolyzed gelatin: 35.7 g
Sorbitol: 35.7 g
Medium 199: 11.06 g
Sodium phosphate buffer, 1 M, pH 6.0: 100 ml
Distilled water: q.s.

This diluent is described in greater detail as formulation B of U.S. Pat. No. 4,147,772, the disclosure of which is hereby incorporated by reference. To make a single dose vaccine, 0.7 ml of the diluted liquid (0.1 ml concentrate and 0.3 ml diluent) is filled into each of 4,000 vials. These vials then are lyophilized simultaneously. Thus, in a single run the water in 4,000 vials each containing 0.7 ml (a total amount of 2,800 ml), must be sublimed. This is accomplished in the following manner.

The vials are precooled to $-50°$ C. and loaded on the shelves of a lyophilizer. The lyophilization chamber is evacuated and the temperature raised to $-20°$ C. and held at that temperature until the temperature of the vials rises to $-30°$. From this point on, the temperature is raised at a rate of 5° C./hour until the temperature of the vials is equal to $-5°$ C. Then the temperature in the chamber is raised to 30° C. and held at that temperature until all the vails have a temperature equal to or above 25° C. for a minimum of 5 consecutive hours. The lyophilization temperature is then swept with Argon and the vials are stoppered. The total lyophilization cycle takes 40 hours.

In an attempt to reduce lyophilization time, 720 ml of the starting measles concentrate is diluted to 1,600 ml by addition of 880 ml of the above-mentioned diluent whose ingredients are increased by a factor of 2.4, in order not to change the chemical composition of the reconstituted vaccine. The diluted liquid is filled into each of 4,000 vials, 0.4 ml/vial. In this case the total amount of water to be sublimed is 1,600 ml. A heavy precipitate is formed in the liquid diluent rendering the liquid unhomogeneous and unsuitable for lyophilization.

EXAMPLE 2

A. Preparation of Stabilizer

A stabilizing medium is prepared by mixing the following ingredients:

| Ingredients | Amount |
| --- | --- |
| Partially hydrolyzed gelatin, 25% aqueous solution (Sol-U-Pro) | 343 ml |
| Sorbitol (powder) | 85.7 g |
| 10 × Concentrated Medium 199 | 148 ml |
| NaHCO$_3$, 2.8% | 66.4 ml |
| DGP solution | 1.5 ml |
| Phenol Red, 2% | 0.75 ml |
| Distilled water | q.s. to 760 ml |

Mixing is continued until all of the ingredients are in solution. The mixture is sterilized by filtration through a 0.22 M filter at 2–2.5 atmospheres and stored at 2°–8° C.

DGP solution is prepared by mixing together the following fractions 1, 2 and 3.

| | |
|---|---|
| 1 | |
| Cysteine HCl | 0.1 g |
| Glutathione | 0.05 g |
| Ascorbic acid | 0.05 g |
| $H_2O$ | 0.9 liter |
| 2 | |
| Vitamin A, crystalline | 0.025 g |
| Ethanol, USP | 10.0 ml |
| Polyoxyethylene (20) sorbitan monooleate, USP | 5.0 ml |
| $H_2O$ | 8.5 ml |
| 3 | |
| Adenosine triphosphate (ATP) | 10.0 g. |

B. Preparation of Virus Dilution

1 M sodium phosphate buffer, pH 6.2, 240 ml, is added to the solution prepared in A, and 880 ml of the resulting preparation is mixed with 720 ml of measles virus concentrate and 44 mg Neomycin. The final solution is filled in vials at 0.40 ml dose level (no precipitation occurs) and frozen at −50° C. or lower.

C. Lyophilization

The frozen vials are allowed to equilibrate in a lyophilizer to −50° C. The pressure is then reduced to 40μ. Enough helium is introduced to raise the pressure to 120–150μ. The temperature is raised to −10° C. over a period of one hour, held at this level for one hour, then raised to 25° C. over a period of one hour and held at this temperature for 2 hours. The pressure is then reduced to 40μ for an additional 2 hours after which the lyophilization chamber is swept with Argon and the vials are stoppered. The vials are reconstituted for use by addition of 0.7 ml of water for injection.

What is claimed is:

1. A method for preparing an aqueous live virus composition for subsequent lyophilization comprising
   preparing a concentrated virus-diluent composition having a volume substantially less than the volume to which it is to be reconstituted at time of use, wherein the virus-diluent composition contains a phosphate salt which phosphate salt has been added to the diluent as the final ingredient.

2. A method according to claim 1 wherein after the phosphate salt is added to the diluent as the final ingredient of the diluent, the complete diluent is then added to the concentrated virus.

3. A method according to claim 1 wherein the prelyophilization volume is less than about 75% of the reconstituted volume.

4. A method according to claim 1 wherein the virus is measles virus.

5. A method according to claim 4 wherein the prelyophilization volume is less than about 75% of the reconstituted volume.

6. A method according to claim 2 wherein the virus is measles virus.

* * * * *